(12) United States Patent
Babineau

(10) Patent No.: US 12,414,922 B2
(45) Date of Patent: Sep. 16, 2025

(54) SYSTEMS AND METHODS FOR TROCHE PRODUCTION

(71) Applicant: Thomas Babineau, Blaine, MN (US)

(72) Inventor: Thomas Babineau, Blaine, MN (US)

( * ) Notice: Subject to any disclaimer, the term of this patent is extended or adjusted under 35 U.S.C. 154(b) by 600 days.

(21) Appl. No.: 17/665,392

(22) Filed: Feb. 4, 2022

(65) Prior Publication Data

US 2022/0249384 A1 Aug. 11, 2022

Related U.S. Application Data

(60) Provisional application No. 63/146,311, filed on Feb. 5, 2021.

(51) Int. Cl.
*A61K 9/20* (2006.01)
*A61J 3/06* (2006.01)
*A61K 9/00* (2006.01)

(52) U.S. Cl.
CPC ............... *A61K 9/2095* (2013.01); *A61J 3/06* (2013.01); *A61K 9/0056* (2013.01)

(58) Field of Classification Search
CPC ........ A61K 9/2095; A61K 9/0056; A61J 3/06
See application file for complete search history.

(56) References Cited

U.S. PATENT DOCUMENTS

2012/0049412 A1 3/2012 Middelbeek et al.

OTHER PUBLICATIONS

Jacques (Tablet Scoring: Current Practice, Fundamentals, and Knowledge Gaps; Appl. Sci. 2019, 9, 3066 (Year: 2019).*

* cited by examiner

*Primary Examiner* — Aradhana Sasan
(74) *Attorney, Agent, or Firm* — UNDERWOOD & ASSOCIATES, LLC

(57) ABSTRACT

A troche/rapidly dissolving tablet production system includes a temperature-controlled heating plate, a score plate configured to confront said heating plate, and a cavity plate configured to confront said scoring plate, said cavity plate comprising a plurality of cavities.

19 Claims, 4 Drawing Sheets

SYSTEMS AND METHODS FOR TROCHE PRODUCTION

CROSS REFERENCE TO RELATED APPLICATIONS

This application claims priority to and the benefit under 35 USC § 119(e) of U.S. Provisional Patent Application No. 63/146,311, filed on Feb. 5, 2021, the contents of which are incorporated by reference in their entirety as if fully set forth herein.

STATEMENT REGARDING FEDERALLY SPONSORED RESEARCH OR DEVELOPMENT

None.

TECHNICAL FIELD

This disclosure relates to systems and methods for the production of rapid-dissolve tablets and troches.

BACKGROUND

Troches are oral vehicles used for the delivery of many types of medicinal compounds. Some troches are utilized for slow- or extended-release of medicinal or pharmaceutical compounds, such as lozenges used to soothe colds and sore throats. Other troches can be formulated to release their medicinal payload quickly.

Rapid-dissolve tablets (RDT's) are similar to troches, with the exception that, as the name implies, they are formulated to dissolve quickly, thereby expediting release of medicine, pharmacological compounds or other ingredients to the user.

Troches are commonly intended to be dissolved under the tongue of a user. In many cases, troches are designed to deliver an active ingredient directly into the bloodstream, bypassing the digestive system and allowing the active ingredient to be introduced into the circulatory system rapidly. The mouth contains a high number of blood vessels very close to the surface of the inner cheeks and below the tongue. Utilizing a troche allows an active ingredient to bypass organs in the human body that may metabolize, alter or reduce the efficacy of the ingredient, such as the liver and kidneys. While some of the active ingredient may be swallowed, it is believed that an adequate amount of active ingredient still enters the bloodstream at a relatively rapid rate.

Troches and RDT's can be especially useful for those who suffer from irritable bowel syndrome or other digestive sensitivities to medications, or those who have difficulty swallowing. Without wishing to be bound by theory, it is generally known that any medication that can be encapsulated or integrated into a pill form can be delivered by a troche or RDT with the same or even higher degree of absorption and efficacy.

The traditional process of making RDT's and troches generally includes compounding or formulating an active ingredient such as a pharmaceutical with an inert, dissolvable carrier compound or "base." The mixture of active ingredient and carrier compound are then placed into molds having the shape and form of the desired product; usually one that can be taken orally and fit under the tongue while the troche or RDT dissolves. Flavor enhancers can also be used. The mixture of active ingredient and carrier are then typically baked in a convection oven according to the solidification properties of the carrier compound. Producing a desired troche or RDT can require careful attention to heating parameters so as not to cause chemical or physical reactions with the pharmaceutical.

Traditional ways of producing RDTs and troches, while effective, requires a great deal of attention to cleanliness and sterility. In particular, traditional methods require convection ovens that are bulky and occupy valuable pharmacy space; they are also expensive to buy and to operate, often times requiring special electrical considerations. Convection ovens have a tendency to heat up the pharmacy and compete with air conditioning, reducing the efficiency of HVAC systems and can be a source of burn liability to operators and staff. The powders used in producing RDT's can easily become airborne, which is a serious consideration when complying with regulatory standards such as USP <800>. Lastly, traditional molds utilize unreliable coated metal molds that often times require a hammer to remove doses. Molds made from plastics can off-gas volatile chemicals when baked, which can introduce toxins into the troche or RDT, and also the atmosphere around the oven.

Accordingly, a system for creating a large number of troche or RDT's that is compact and easily used under a containment hood, that promotes regulatory compliance (e.g., USP <800>), provides delicate, precise heating controls while not requiring special electrical connections, is made with non-stick materials for ease of removal and is versatile to produce troches, RDT's, chews and other products is a unmet need in the art.

SUMMARY

In one general aspect, a system for the production of troches and rapid-dissolve tablets is disclosed. In one exemplary embodiment, the system includes a temperature-adjustable heat plate, a score plate, the score plate including an array of raised scoring marks, and a cavity plate, the cavity plate including an array of cavities equal in number and arrangement to the array of raised scoring marks. The score plate is configured to be placed atop the heat plate in a confronting relationship, and the cavity plate is configured to be placed atop the scoring plate in a confronting relationship.

In one embodiment, the system further includes a thermostat configured to provide temperature regulation of the heat plate.

In one embodiment, each cavity of the array of cavities has a volume of about one (1) milliliter when the cavity plate and the score plate are in a confronting relationship.

In one embodiment, each of the raised scoring marks defines a scoring pattern allowing a troche or rapid-dissolve tablet produced by the system to be separated into one-half, one-quarter or one-eighth component pieces. A first example of a scoring pattern is a plus (+) shape; a second example of a scoring pattern is a minus (−) shape.

In one embodiment, the cavity plate includes a raised lip about its outer perimeter.

In one embodiment, the system further includes a tamper plate. The tamper plate includes a flat plate surface and a plurality of protrusions extending from the flat plate surface. The plurality of protrusions matches the array of cavities in number. In a related embodiment, each protrusion of the plurality of protrusions has a length and width dimension, each parallel with the flat plate surface, the length and width dimensions being selected to allow each protrusion to fit within each cavity of the array of cavities. In a further related embodiment, each protrusion further includes a depth dimension, the depth dimension being less than the depth of each cavity of the array of cavities when the cavity plate is in a confronting relationship with the score plate.

In one embodiment, the cavity plate is formed of a non-stick material.

In one embodiment, the system further includes a powder dam, wherein the power dam includes a frame structure configured to surround the array of cavities.

In one embodiment, the cavity plate and the score plate are formed of a non-stick material such as coated aluminum.

In a second general aspect, a method is disclosed for the production of a plurality of troches. In one embodiment, the method includes providing the system according to the first general aspect described above, providing a compounded formula including a liquid troche base and an active ingredient, warming the heating plate to a temperature sufficient to maintain the compounded formula in liquid form, placing the score plate atop the heating plate, placing the cavity plate atop the score plate, filling the array of cavities of the cavity plate with the compounded formula and allowing the heating plate to cool. In one embodiment, the active ingredient is a pharmaceutical agent.

In a third general aspect, a method is disclosed for the production of a plurality of rapid-dissolve tablets. In one embodiment, the method includes providing the system according to the first general aspect described above. The method further includes providing a powder compounded formula including a powdered base matrix for rapidly-dissolving tablets and an active ingredient, placing the cavity plate atop the score plate, filling the array of cavities of the cavity plate with the powder compounded formula, placing the score plate and the cavity plate atop the heating plate and heating the heating plate until the compounded formula solidifies.

In one embodiment, the method further includes providing a tamper plate; the tamper plate including a flat plate surface and a plurality of protrusions extending from the flat plate surface; the plurality of protrusions matching the array of cavities in number and arrangement; and compressing the compounded formula within the array of cavities utilizing the tamper plate.

In one embodiment, the method further includes placing the tamper plate atop the cavity plate until the compounded formula solidifies. The active ingredient can be a pharmaceutical agent.

Certain advantages of the systems and methods include, specific to RDT production: compactness of the system in that can easily be used under containment hood; the ability to produce a high number of RDT's at once, e.g., the ability to produce 196×750 mg RDT's; promotes USP <800> compliance; the ability to digitally control temperature during formation; precision aluminum plates offer fast heating and cooling, even heat distribution which is lightweight, and easy to clean; and the ability to increase capacity by adding additional plates; among others.

Certain advantages of the systems and methods include, specific to troche production: compactness of the system in that it can easily be used under containment hood; the ability to produce a large number of troches per run, e.g., 196×1 mL cavities; promotion of USP <800> compliance; a programmable, digital thermostat for precise temperature control; no special electrical requirements; precision aluminum plates offer fast heating and cooling, even heat distribution, lightweight, and easy to clean; providing a heated work surface to allow for extended troche working time; minimal troche compound residual ingredients common with mat-style silicon molds; no troche polishing required; and the ability to increase yield simply by adding additional plates; among others.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DESCRIPTION OF DRAWINGS

The present embodiments are illustrated by way of the figures of the accompanying drawings, which may not necessarily be to scale, in which like references indicate similar elements, and in which.

DETAILED DESCRIPTION OF ILLUSTRATIVE EMBODIMENTS

Figure 1:
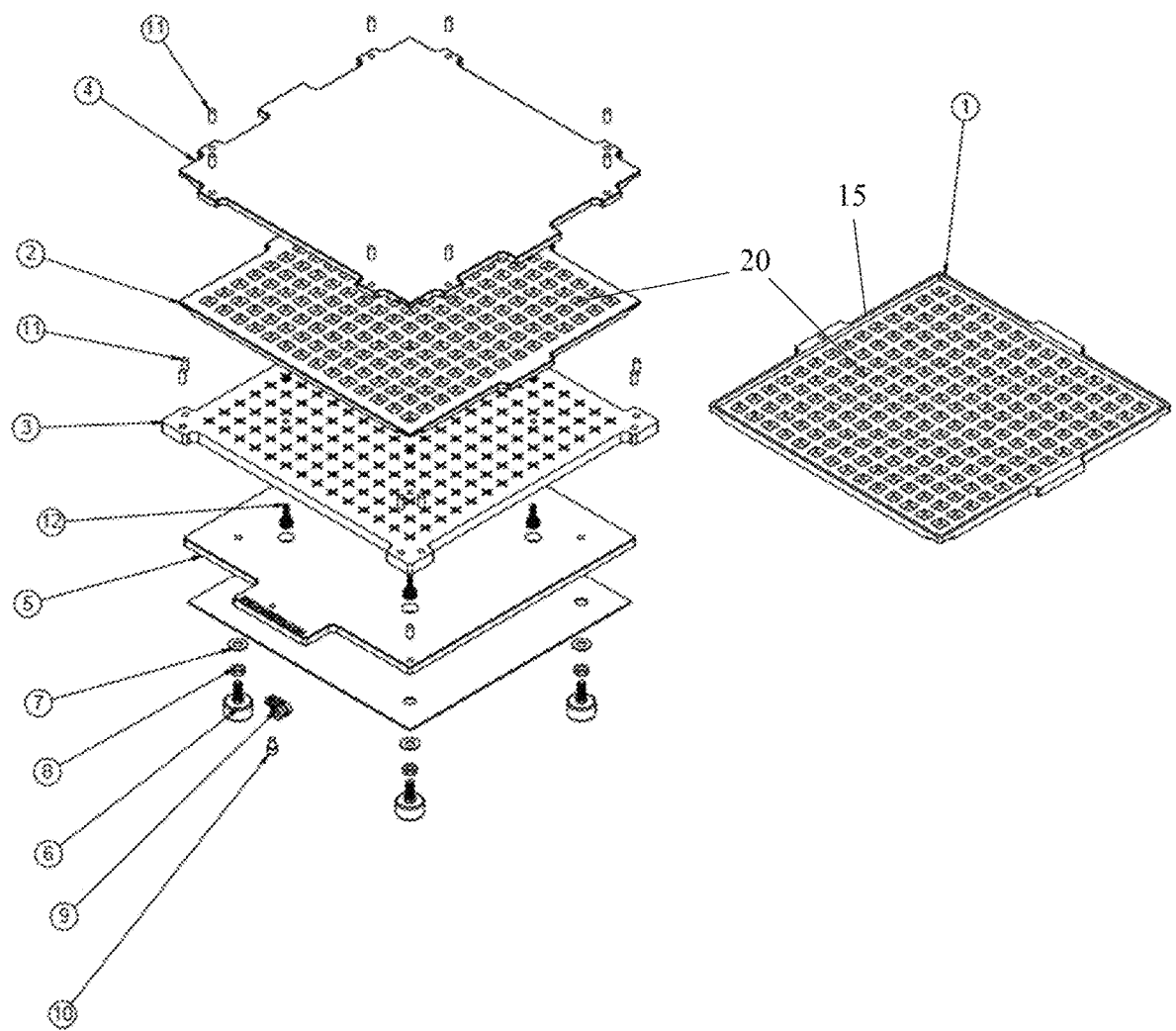
FIG. 1 is an exploded view of a troche/RDT molding system according to one embodiment.
Figure 2:
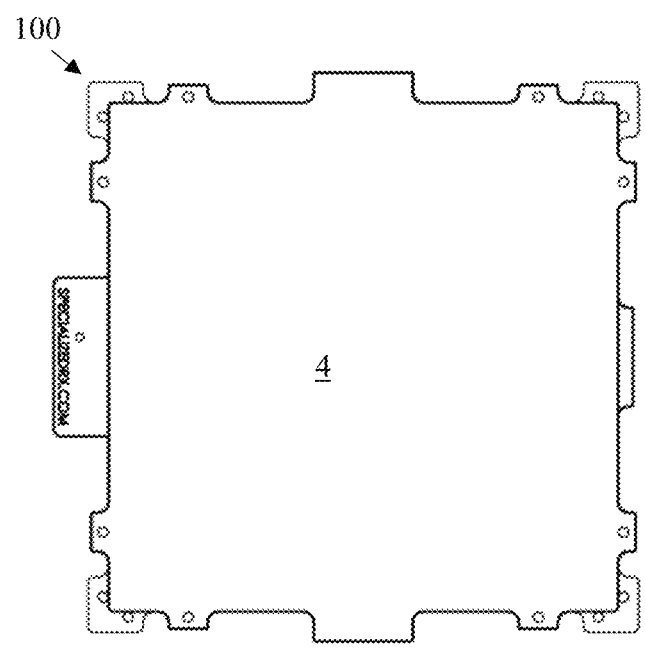
FIG. 2 is a top view of the troche/RDT molding system of FIG. 1 as assembled.
Figure 3:
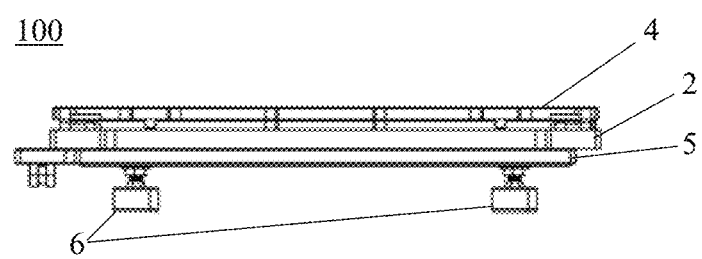
FIG. 3 is a side view of the troche/RDT molding system of FIG. 1 as assembled.
Figure 4:
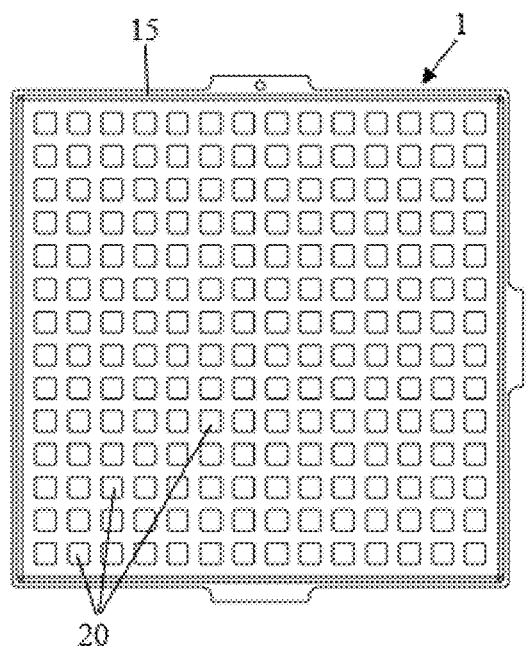
FIG. 4 is a top view of a cavity plate of a troche/RDT molding system according to one embodiment.

FIG. 1 shows an exploded view, and FIGS. 2-3 show an assembled view of a troche/rapidly dissolvable tablet (RDT) molding system (hereinafter 'system') 100 according to one embodiment. In this embodiment, the system 100 includes a cavity plate 1 with an overflow lip 15 disposed about its perimeter. FIG. 4 shows a top plan view of the cavity plate 1. The cavity plate 1 includes a plurality of cavities 20 (in this example, one hundred ninety-six cavities) for receiving a compounded formulation of an active ingredient and base. Troche bases usually consist of a sweetened blend of polyethylene glycols. In this embodiment, each cavity 20 holds a volume of about one milliliter, e.g., 0.7 mL, 0.8 mL, 0.9 mL, 1.0 mL, 1.1 mL, 1.2 mL, 1.3 mL, although other volumes can be used that are appropriate for troches. When utilizing the system 100 for RDT production, the cavities are suitable to provide a 750 mg RDT.

The system 100 further includes an optional cavity plate 2 that does not include an overflow lip, a score plate 3, a tamper plate 4, a heating plate 5, a plurality of leveling feet 6 and a series of hardware for joining the aforementioned components in an assembled configuration (e.g., washers 7, jam nuts 8, vibration dampening loop clamps 9, stainless steel screws 10 that secure the vibration dampening loops, a plurality of dowels 11, a plurality of thumb screws 12 and helical inserts 13).

In this embodiment, the individual cavities 20 of the cavity plate are bottomless. The bottom of each cavity is formed when the cavity plate is placed in confrontation with score plate 3. The score plate 3 is used for producing a score mark onto resultant troches so that they may be broken into half- or quarter-sized doses by the user. In this embodiment, the score plate 3 includes raised score marks in the shape of plus (+) symbols; however, it should be understood that the score marks can be any desired shape and size.

In this embodiment, the cavity plate 2 rests on the score plate 3 when the system 100 is in an assembled and operative configuration. When a troche formulation is poured into the troche cavities 20 of the cavity plate 2, the score marks are transferred to the resulting troches. After the troches solidify, they may be cleanly broken into quarter- or half-size doses. It should be understood that a score mark can be used for dividing troches into other fractional sizes and is not limited to half- or quarter-sized portions.

In this embodiment, the system 100 can be used for making troches on a benchtop setting or in a clean containment hood. One advantage of this approach is that heating plate 5 can be used to heat the cavity plates 1 or 2 without need for a convection oven, which is common in the troche industry. This advantage results in that the troches can be produced in a containment hood, e.g., a controlled environment which can reduce contamination. When current troche methods are used using a convection oven, active drug product powders can escape into the pharmacy which can result in contamination of surfaces, other pharmaceuticals and products, and can be a violation of USP codes.

Figure 5:
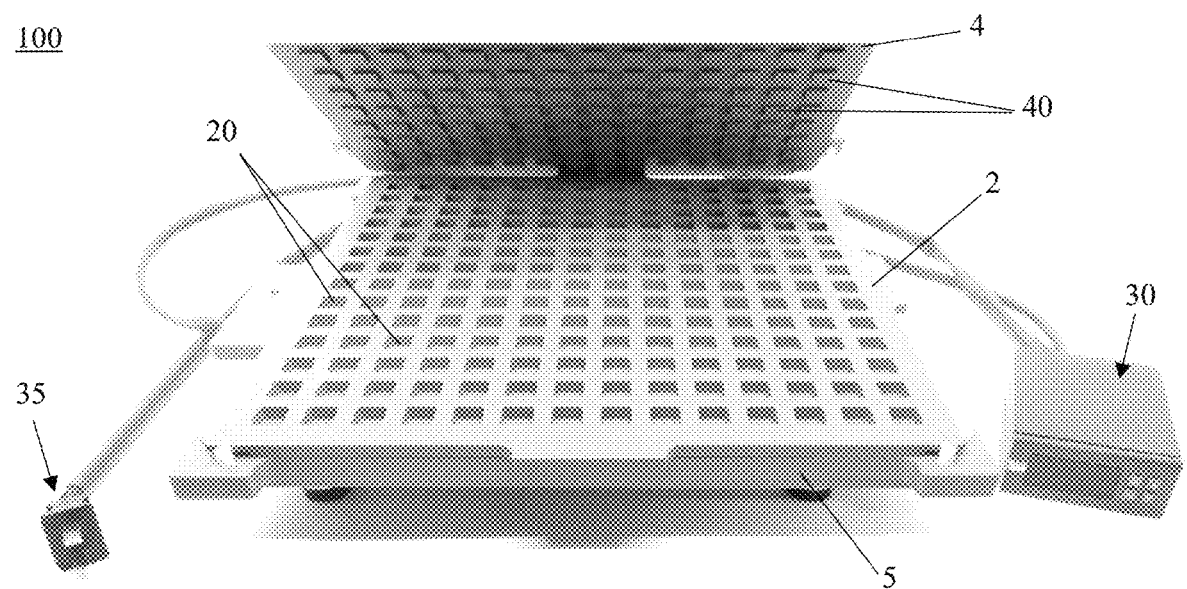
FIG. 5 is a perspective view of the troche/RDT molding system of FIG. 1 according to one embodiment.

Referring to FIG. 5, a perspective view of the system 100 is shown in an assembled configuration. In this embodiment, a digital temperature controller 30 is used to provide controllable temperature regulation of the cavity plate 1 or 2 (depending on which is used) by way of heating plate 5. In this embodiment, power for the digital temperature controller 30 is provided by way of plug 35 which can be adapted or configured for use with residential or commercial power supply. The digital temperature controller 30 is programmable and has a feedback loop via at least one thermocouple configured to measure the temperature of the heating plate 5. Accordingly, a desired temperature can be set by way of the controller 30; because the cavity plate 1 or 2 rests on the heating plate, the cavity plate 1 or 2 will become warmed by the heating plate 5.

Still referring to FIG. 5, in this embodiment, the system can be used for preparing RDT's from powdered ingredients. Tamper plate 4 includes an array of protrusions matching the array of cavities 20. Each protrusion 40 has a length and width parallel with the top 45 of the tamper plate 4 sufficient to allow each protrusion to fit within a corresponding cavity 20. The depth of each protrusion 40 is less than the depth of each cavity 20, thereby allowing the tamper plate to be used for compacting powdered RDT ingredients within the cavities 20.

In this embodiment, the system 100 can be used to make troches by way of the following example. First, the heating plate 5 can be heated to a temperature sufficient to keep a chosen troche base and any pharmaceuticals or active ingredients disposed therein in liquid form. Next, the score plate 3 and cavity plate 1 or 2 can be placed onto the heating plate 5. In practice, it can be beneficial to allow the heating plate and the cavity plate 1 or 2 to achieve thermal equilibrium with the heating plate.

Next, a liquid troche base can be poured onto the cavity plate 1 or 2, filling all of the cavities 20. A spatula or scraper can be used to wipe excess troche base from the cavity plate 1 or 2. In the case that cavity plate 1 is used, the overflow lip 15 can be useful in containing excess troche base on the cavity plate. In one embodiment, the cavity plate 1 or overflow lip 15 can include a recess enabling one to collect excess troche base therein or allow the excess troche base to be poured off.

Next, once the troche base is level across the cavities 20 and excess troche base has been removed, the heat plate can be turned off to allow it to return to room temperature. After the troche has cooled and solidified, the cavity plate 1 or 2 can be removed from the heating plate and the individual troches removed.

Figure 6:
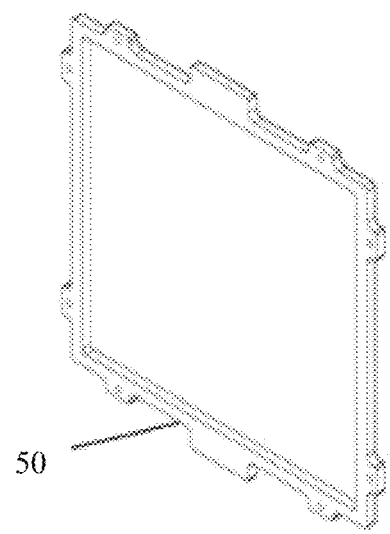
FIG. 6 is a powder dam, according to one embodiment.

In this embodiment, the system 100 can be used to make RDT's by way of the following example. First, on a flat, clean surface the cavities 20 are filled with the powder mixture. To aid in filling all of the cavities, and to ensure consistency, a powder scraper can be used. Excess powder should be removed. Referring briefly to FIG. 6, the use of a powder dam 50 can assist in proper powder spreading. The powder dam 50 is similar to a frame that provides a border around the array of cavities 20 on the cavity plate, preventing excess powder from spilling over the edge of the cavity plate 2 and allowing better management of powder when filling the cavities.

Next, the powder in the cavities 20 is compacted. Referring to FIG. 5, tamper plate 4 includes protrusions, as described herein, for the purpose of compacting powder into the cavities 20. In general, it may take multiple iterations of adding RDT powder to the cavity plate 1 or 2 and compressing the powder with the tamper plate in order to fill each cavity 20 completely and compactly.

Next, the heating plate 5 is pre-heated to a desired temperature, depending on the RDT formula requirements. Next, the score plate 3 is placed on the heating plate, and the cavity plate 2 is placed on top of the score plate 3. The tamper plate 4 is then inverted and placed on top of the cavity plate 2, so that the protrusions 40 of the tamper plate 4 confront the filled cavities 20 of the cavity plate 2. Having the tamper plate 4 atop the cavity plate 2 can aid in retaining heat within the cavities, resulting in a more uniform heating process.

Once the heating cycle has finished, per the RDT formulation used, the heat is turned off and the tamper plate 4 is removed. Before the score plate 3 and the cavity plate 2 are separated, they are removed together and allowed to cool slightly at room temperature. The individual RDT's can then be removed from the cavity plate.

A number of illustrative embodiments have been described. Nevertheless, it will be understood that various modifications may be made without departing from the spirit and scope of the various embodiments presented herein. Accordingly, other embodiments are within the scope of the following claims.

What is claimed is:

1. A system for the production of troches and rapid-dissolve tablets, comprising:
   a temperature-adjustable heat plate configured to apply controlled heat to a scoring surface;
   a score plate positionable atop said heat plate, said score plate comprising an array of raised scoring marks formed on an upper surface thereof and further comprising alignment features along its perimeter; and
   a cavity plate, said cavity plate comprising an array of cavities arranged to correspond with said array of raised scoring marks, said cavity plate being configured to be placed atop said scoring plate in a confronting relationship such that each cavity is axially aligned with a corresponding scoring mark;

wherein each of said cavities is open at a lower end and closed at an upper end;

wherein the alignment features of the score plate are configured to ensure fixed registry between said cavity plate and said score plate to maintain the positioning of each scoring mark relative to each cavity; and wherein said raised scoring marks are configured to contact a lower surface of a liquid or molten compounded formulation placed within said cavities and to impart one or more score lines into said formulation prior to solidification, thereby forming scored troches or tablets without post-formation cutting or modification.

2. The system of claim 1, further comprising a thermostat configured to provide temperature regulation of said heat plate.

3. The system of claim 1, wherein each cavity of said array of cavities has a volume of about one (1) milliliter when said cavity plate and said score plate are in a confronting relationship.

4. The system of claim 1, wherein each of said raised scoring marks defines a scoring pattern configured to facilitate separation of a troche or rapid-dissolve tablet into one-half, one-quarter or one-eighth portions after solidification along pre-formed score lines.

5. The system of claim 4, wherein said scoring pattern is a plus (+) shape.

6. The system of claim 4, wherein said scoring pattern is a minus (−) shape.

7. The system of claim 1, further comprising a tamper plate, said tamper plate comprising:
a flat plate surface; and
a plurality of protrusions extending from said flat plate surface;
wherein each of said protrusions is configured to compress powdered material within said cavities without disturbing the score lines imparted by said score plate.

8. The system of claim 7, wherein each protrusion of said plurality of protrusions has a length and width dimension, each parallel with said flat plate surface, said length and width dimensions being selected to allow each protrusion to fit within a corresponding cavity of said array of cavities.

9. The system of claim 8, wherein each protrusion further comprises a depth dimension, said depth dimension being less than the depth of each cavity of said array of cavities when said cavity plate is in a confronting relationship with said score plate.

10. The system of claim 1, wherein said cavity plate is formed of a non-stick material.

11. The system of claim 1, further comprising a powder dam, wherein said powder dam comprises a removable frame structure configured to surround said array of cavities and inhibit lateral migration of powder during filling or tamping.

12. A method for the production of a plurality of troches, comprising:
providing the system according to claim 1;
providing a compounded formula comprising a liquid troche base and an active ingredient;
warming said heating plate to a temperature sufficient to maintain said compounded formula in liquid form;
placing said score plate atop said heating plate;
placing said cavity plate atop said score plate;
filling said array of cavities of said cavity plate with said compounded formula; and
allowing said heating plate to cool.

13. The method of claim 12, wherein said active ingredient is a pharmaceutical agent.

14. A method for the production of a plurality of rapid-dissolve tablets, comprising:
providing the system according to claim 1;
providing a powder compounded formula comprising a powdered base matrix for rapidly-dissolving tablets and an active ingredient;
placing said cavity plate atop said score plate;
filling said array of cavities of said cavity plate with said powder compounded formula;
placing said score plate and said cavity plate atop said heating plate; and
heating said heating plate until said compounded formula solidifies.

15. The method of claim 14, further comprising:
providing a tamper plate, said tamper plate comprising:
a flat plate surface; and
a plurality of protrusions extending from said flat plate surface;
wherein said plurality of protrusions matches said array of cavities in number and arrangement; and
compressing said compounded formula within said array of cavities utilizing said tamper plate.

16. The method of claim 15, further comprising placing said tamper plate atop said cavity plate until said compounded formula solidifies.

17. The method of claim 14, wherein said active ingredient is a pharmaceutical agent.

18. The system of claim 1, wherein said raised scoring marks are oriented in a uniform direction across said score plate and said cavity plate comprises a keyed feature configured to be received in a corresponding slot on said score plate, thereby ensuring a fixed rotational orientation between said plates during use.

19. The system of claim 7, wherein said tamper plate is configured to compress a powdered formulation within said array of cavities while maintaining visibility of score lines imparted by said score plate.

\* \* \* \* \*